United States Patent [19]

Sullivan

[11] Patent Number: 5,688,765
[45] Date of Patent: Nov. 18, 1997

[54] OCULAR THERAPY IN SJOGREN'S SYNDROME USING TOPICALLY APPLIED ANDROGEN SOR TGF-β

[75] Inventor: David A. Sullivan, Acton, Mass.

[73] Assignee: The Schepens Eye Research Institute, Inc., Boston, Mass.

[21] Appl. No.: 477,301

[22] Filed: Jun. 7, 1995

Related U.S. Application Data

[63] Continuation-in-part of Ser. No. 124,842, Sep. 21, 1993, Pat. No. 5,620,921, which is a continuation of Ser. No. 871,657, Apr. 21, 1992, abandoned.

[51] Int. Cl.$^6$ .................................................. A61K 37/00
[52] U.S. Cl. ................................. 514/12; 514/2; 514/912
[58] Field of Search ............................. 514/2, 12, 912

[56] References Cited

PUBLICATIONS

Sato et al., "Impact of Androgen Therapy in Sjögren's Syndrome: Hormonal Influence on Lymphocyte Populations and Ia Expression in Lacrimal Glands of MRL/Mp-lpr/lrp Mice," Invest. Opht. & Vis. Science 33:2537–2545 (1992).
Sato et al., "Comparative Influence of Steroid Hormones and Immunosuppressive Agents on Autoimmune Expression in Lacrimal Glands of a Female Mouse Model of Sjögren's Syndrome," Inves. Opht. & Vis. Sci. 35:2632–2642 (1994).
Rocha et al., "Effect of Androgen Analogue Treatment and Androgen Withdrawal on Lacrimal Gland Inflammation in a Mouse Model (MRL/Mp-lpr/Ipr) of Sjögren's Syndrome," Regional Immunology 6:1–8 (1995).
Sullivan et al., "Influence of Steroids and Immunosuppressive Compounds on Tear IgA Levels in a Mouse Model of Sjögren's Syndrome," Invest. Opht. & Vis. Science, p. 845.
Sullivan et al., "Potential Therapeutic Approach for the Hormonal Treatment of Lacrimal Gland Dysfunction in Sjögren's Syndrome," Clin. Immunol. and Immunopath. 64:9–16 (1992).

Ono et al., "Analysis of Androgen Receptors and Cytokines in Lacrimal Glands of Mouse Model of Sjögrens' Syndrome," Invest. Opht. & Vis. Science 35:1793 (1994).
Clark et al., "Mechanisms of Action of Steroid Hormones," pp. 35–90.
Mountz et al., "Murine models for systemic lupus erythematosus and Sjögren's Syndrome," Current Science ISSN pp. 738–756 (1991).
Sibbitt, "Ongogenes, Growth Factors, and Autoimmune Diseases," Anticancer Research 11:97–114 (1991).
Firestein, "Cytokines in Autoimmune Diseases," Concepts Immunopathol. 8:129–160 (1992).
Kroemer et al., "Cytokines and Autoimmune Disease," Clin. Immunol. & Immunopath. 61:275–295 (1991).
Dinarello, "Interleukin–1 and tumor necrosis factor: effector cytokines in autoimmune diseases," seminars in Immunology 4:133–145 (1992).
Mountz et al., "Murine models of autoimmune disease," Current Science ISSN pp. 621–629 (1992).
Wahl, "Transforming Growth Factor β: The Good, the Bad, and the Ugly," Journ. of Exp. Med. 180:1587–1590 (1994).
Wakefield et al., "The Role of cytokines in the Pathogenesis of Inflammatory Eye Disease," Cytokine 4:1–5 (1992).
Rosenbaum, "Cytokines: The Good, The Bad, and The Unknown," Invest. Ophth. & Vis. Science 34:2389–2391 (1993).
Fox et al., "Pathogenesis of Sjögren's Syndrome," Rheumatic Disease Clinics of North America 18:517–539 (1992).

Primary Examiner—Zohreh Fay
Attorney, Agent, or Firm—Weingarten, Schurgin, Gagnebin & Hayes LLP

[57] ABSTRACT

The topical application to the ocular surface or adjacent regions of the eye of a preparation containing a therapeutic amount of an androgen or androgen analogue or a therapeutic amount of TGF-β is disclosed as a method of relieving the chronic and acute manifestation of dry eye symptoms in Sjögren's syndrome. Measurement of the increased tear levels of TGF-β is disclosed as a diagnostic test to monitor the therapeutic effect of topical treatment with androgen or androgen analogues.

4 Claims, No Drawings

OCULAR THERAPY IN SJOGREN'S SYNDROME USING TOPICALLY APPLIED ANDROGENSOR TGF-β

This application is a continuation-in-part of Sullivan, U.S. patent application Ser. No. 08/124,842, filed Sep. 21, 1993 now U.S. Pat. No. 5,620,921, which was a continuation under 37 CFR 1.62 of Ser. No. 07/871,657, filed Apr. 21, 1992 now abandoned, the whole of which are hereby incorporated by reference herein.

GOVERNMENT RIGHTS

Part of the work leading to this invention was made with United States Government funds under Grant No. EY05612 from the National Institutes of Health. Therefore, the U.S. Government has certain rights in this invention.

FIELD OF THE INVENTION

This invention relates to treating keratoconjunctivitis sicca (KCS), especially as manifested in Sjögren's syndrome.

BACKGROUND OF THE INVENTION

The preocular tear film plays an essential role in the maintenance of corneal integrity, the protection against microbial challenge and the preservation of visual acuity (1). These functions, in turn, are critically dependent upon the stability, tonicity and/or composition of the tear film structure, which includes an underlying mucin foundation, a substantial, middle aqueous component and an overlying lipid layer (1,2). Alteration, deficiency or absence of the tear film may lead to intractable desiccation of the corneal epithelium, ulceration and perforation of the cornea, an increased incidence of infectious disease, and ultimately, severe visual impairment and blindness (2,3).

Throughout the world, countless individuals suffer from tear film dysfunctions, which are collectively diagnosed as keratoconjunctivitis sicca (KCS) or, simply, dry eye (1,2). These lacrimal abnormalities may be subdivided into four general categories: (a) aqueous tear deficiencies, which are most frequently responsible for dry eye states, originate from lacrimal gland disorders and include autoimmune disease, congenital alacrima, paralytic hyposecretion or excretory duct obstruction; (b) mucin deficiency, which is observed in various conjunctival cicatrization conditions, such as Stevens-Johnson syndrome, trachoma, pemphigoid, thermal and chemical burns, as well as hypovitaminosis A; (c) lipid abnormalities, which may occur during eyelid inflammation (e.g. chronic blepharitis); and (d) diminished eyelid function (1).

By far, the greatest single cause of KCS worldwide, excluding those countries wherein trachoma remains epidemic, is Sjögren's syndrome (2). This syndrome, which is the second most common autoimmune disease (7,14), occurs almost exclusively in females and is characterized by an insidious and progressive lymphocytic infiltration into the main and accessory lacrimal glands, an immune-mediated, extensive destruction of lacrimal acinar and ductal tissues and the consequent development of persistent KCS (7–10). In primary Sjögren's syndrome, which afflicts about 50% of the patient population, the disease is also associated with an immunological disruption of the salivary gland and pronounced xerostomia. In secondary Sjögren's, the disorder is accompanied by another disease, which is most often rheumatoid arthritis and less frequently systemic lupus erythematosus (SLE), scleroderma, polymyositis, polyarteritis nodosa, Hashimoto's thyroiditis, chronic hepatobiliary disease, chronic pulmonary fibrosis, purpura hyperglobulinemia or Raynaud's phenomenon (2,11). During the course of Sjögren's syndrome, autoimmune sequelae may also encompass focal lymphocytic adenitis of eccrine and mucosal glands, biliary cirrhosis, sclerosing cholangitis, pancreatitis, atrophic gastritis, interstitial nephritis and pneumonitis, peripheral vasculitis, B cell lymphoma and a diverse array of central and peripheral nervous system and skeletal muscle complications (12,13).

The etiology of Sjögren's syndrome may be due to the interaction of numerous factors, including those of genetic, endocrine, neural, viral and environmental origin (15,16). However, a potential cause may relate to primary infection by, and reactivation of, Epstein-Barr virus (EBV) and/or cytomegalovirus (CMV) (17–20). These herpes viruses are present in lacrimal and salivary glands of Sjögren's patients (17–20) and may induce the inappropriate HLA-DR expression, T helper/inducer cell activation, B cell hyperactivity and autoantibody production evident in these affected tissues (8). However, whether herpes, or even retroviral (21,22), action represents a cause of, or merely an epiphenomenon in, Sjögren's syndrome remains to be determined (23–25).

At present, a perception is that Sjögren's syndrome may be clinically irreversible (7), an autoimmune disease to be controlled, yet not cured (10). In the scientific literature, reports have suggested that systemic or topical administration of estrogens (4), cyclosporine A (6) or glucocorticoids (26) might alleviate the ocular manifestations of this disorder. However, other studies indicate that such pharmaceutical exposures are ineffective (27–29) and, in fact, may accelerate and/or amplify the disease (28,30). Indeed, estrogen action may be involved in the etiology of Sjögren's syndrome (30,31).

Others have suggested that tear stimulants, such as bromhexine (32) or isobutylmethylxanthine (33), might improve ocular symptoms. These drug effects, though, may be subjective (34), susceptible to tachyphylaxis (4) and/or limited by the requirement for functional and responsive lacrimal tissue (4,35).

It has also been proposed that systemic androgen treatment might provide a potential therapy for Sjögren's syndrome and its associated defects. This proposal is based upon the finding that autoimmune disorders commonly display a sexual dichotomy, with estrogens increasing disease severity in females and androgens suppressing autoimmune sequelae in males (15,16,36–38). In fact, systemic androgen therapy has been utilized to effectively diminish autoimmune expression in animals models of SLE, thyroidiris, polyarthritis and myasthenia gravis (15,38–43), as well as the human condition of idiopathic thrombocytopenic purpura (44). However, research has also demonstrated that the systemic administration of androgens to patients with primary or secondary Sjögren's syndrome or SLE is apparently unable to correct various peripheral manifestations of these disorders (49,54,55,62). In addition, systemic androgen treatment of female patients with Sjögren's syndrome exposes these individuals to possible undesirable side effects, including virilization, menstrual irregularities (e.g., amenorrhea), hepatic dysfunction, edema, hematologic abnormalities, behavioral changes and metabolic alterations. Similarly, chronic treatment of males with systemic androgens has been characterized as dangerous (63), because of the numerous potential side effects. For these reasons, a recent report has indicated that systemic androgen therapy is inappropriate for the treatment of the multiple immune dysfunctions, in Sjögren's syndrome (63).

Others have suggested that anti-viral compounds may represent a new therapeutic approach for ocular disease in Sjögren's syndrome. Researchers have speculated that such compounds may be effective in counteracting the viral (e.g., EBV- and/or CMV)-induced infection in lacrimal tissue, that may possibly precipitate the gland's immune-associated dysfunction (17,19,20). The potential efficacy of this strategy, though, is highly speculative: current scientific information does not show definitively that these viruses are directly involved in the pathogenesis or progression of Sjögren's syndrome (23–25).

Therefore, the currently prescribed, therapeutic approach for the management of KCS in Sjögren's syndrome is the frequent application of artificial tear substitutes, which permit lubrication of the eye's anterior surface (3,4,5,9,10). Unfortunately, this therapy does not represent a cure and does not ameliorate the inherent, ocular immunopathology and resulting KCS associated with this chronic, extremely uncomfortable and vision-threatening disease (3).

SUMMARY OF THE INVENTION

The invention generally features a new approach to the management of KCS in Sjögren's syndrome, the topical application to the eye of a preparation containing a therapeutic amount of an androgen or androgen analogue or a therapeutic amount of TGF-$\beta$. This method of treatment can alleviate the ocular manifestations of Sjögren's syndrome, the special symptoms that cause great distress, while not exposing the patient to the possible undesirable side effects of systemic treatment.

In one aspect, the invention features a method for treating keratoconjunctivitis sicca (KCS) that includes providing a therapeutic agent including a therapeutically effective amount of an androgen or androgen analogue in a pharmaceutically acceptable substance, and administering said therapeutic agent topically to the ocular surface or immediate vicinity of an eye of a patient.

Preferably, the substance is phosphate buffered saline or a carrier substance such as hyaluronate and the androgen or androgen compound has unusual structural features; or the compound is a testosterone, 4,5$\alpha$-dihydrotestosterone, 17$\beta$-hydroxy-5$\alpha$-androstane, or 19-nortestosterone derivative; or the compound is a nitrogen-substituted androgen.

In another aspect, the invention features a similar treatment method wherein the therapeutic agent includes TCF-$\beta$.

The invention also features measurement of the increased tear levels of TGF-$\beta$ to provide a diagnostic test to monitor the therapeutic effect of topical treatment with androgen analogues.

Other features and advantages of the invention will be apparent from the following description of the preferred embodiments thereof and from the claims.

DESCRIPTION OF THE PREFERRED EMBODIMENTS

Various androgen compounds, as herein discussed, significantly reduce the magnitude of lymphocyte infiltration in lacrimal tissue of animal models of Sjögren's syndrome. The nature of androgen action on autoimmune expression in lacrimal tissue appears to be unique and lacrimal gland-specific. It also appears that this hormone effect is not linked to a generalized, systemic anti-inflammatory function.

Building on these new discoveries, the method of the invention involves a rejection of the classical therapeutic approach to treatment for Sjögren's syndrome, a belief that any administered therapeutic agent must be able to control all aspects of the disease. Because steroid hormones (e.g., glucocorticoids), with solubility characteristics analogous to those of androgens, rapidly gain access to adjacent ocular tissues after topical application (78), it is proposed, instead, that topical application of a therapeutic amount of an androgen or androgen analogue to the eye be used to suppress lacrimal gland inflammation and thus treat the debilitating ocular manifestations of this disease. Topical application of a therapeutic androgen can provide for symptomatic relief of the worst ocular symptoms of Sjögren's syndrome without the chance of the patient experiencing the undesirable side effects of systemic administration. Furthermore, since the androgen-induced suppression of lacrimal gland inflammation could be mediated through the induction of transforming growth factor-$\beta$ (TGF-$\beta$), a potent immunosuppressive compound, local application of TGF-$\beta$ should also have the same effect.

During the past decade, it has become increasingly recognized that the endocrine system exerts a tremendous, regulatory impact on immunological expression (15,16,36, 37,45,64,65–68,69,70–76). The precise nature of this endocrine control, though, appears to be both cell- and tissue-specific (45). Thus, depending upon the target, the consequence of hormone action may be stimulation, antagonism or inhibition of immune function. Moreover, individual hormone effects on the immune system are often not generalized. Rather, endocrine influence may actually strengthen, diminish or elicit no effect on immunological activity in different tissues (45). Given this background, it is not surprising that the systemic administration of selected hormones (e.g., androgens) is unable to correct all immune defects in multidimensional, autoimmune disorders, such as Sjögren's syndrome or SLE.

Yet, if appropriate endocrine therapy could be targeted to a specific, responsive tissue, hormone action could safely and effectively ameliorate an immunopathology located in that particular tissue. To relieve the symptoms that cause the most ocular distress in Sjögren's syndrome, that targeted, responsive tissue is the lacrimal gland. According to the invention, lipophilic, regulatory hormones applied locally on or adjacent to the ocular surface can act directly on accessory and main lacrimal tissues of Sjögren's syndrome patients and suppress the disease-related glandular inflammation in these tissues. This effect is completely independent of systemic hormone activity. The aim of this immunoendocrine interaction is to: (a) reduce lymphocyte infiltration in adjacent lacrimal tissue and thereby alleviate immune-mediated destruction, and lymphocyte compression, of acinar and ductal cells; (b) permit accessory and/or palpebral lacrimal glands to secrete basal tear volumes; and (c) avoid the side effects that parallel systemic exposure to these hormones. In effect, topical androgen treatment can generate functional regions of lacrimal tissue, thereby enhancing tear output and correcting the dry eye problem.

This pharmaceutical strategy has not been proposed previously. Most probably, this is because the mechanism of androgen action on immune function has been thought to be mediated through, or assisted by, factors from the thymus and hypothalamic-pituitary axis, or else involve direct effects on lymphocytes (37,65,68,77).

Topical ocular application of androgens can relieve the immunopathology of Sjögren's syndrome A critical requirement for the justification of topical ocular application therapy is to demonstrate that androgens suppress lacrimal gland immunopathology in Sjögren's syndrome. In addition, it is important to show that this androgen action is targeted to lacrimal tissue, and independent of generalized, systemic effects. In the examples given below it is shown that all three of these criteria are met, i.e., that androgens do suppress lacrimal gland immunopathology in Sjögren's syndrome, that androgen action is targeted to lacrimal tissue, and that androgen action is independent of generalized, systemic effects.

EXAMPLE I

Androgen influence on lacrimal gland immunopathology in the MRn/Mp-lpr/lpr mouse model of Sjögren's syndrome (47)

The purpose of the following study was to determine whether androgen therapy might inhibit the progression of, or reverse, autoimmune disease in the lacrimal gland after the onset of Sjögren's syndrome. Towards that end, the study utilized adult, female MRL/Mp-lpr/lpr (MRL/lpr) mice, which are an animal model for both Sjögren's syndrome (50,51) and SLE (79,80). Lacrimal tissues of these mice, as in humans, contain multifocal and extensive lymphocytic infiltrates in perivascular and periductal areas, significant glandular disruption and marked fibrosis (50,51).

Physiological or supraphysiological levels of testosterone were administered systemically, and not topically, because the location of the lacrimal gland in mice is inaccessible from the ocular surface. The results demonstrated that androgens exert a significant impact on autoimmune expression in lacrimal glands of MRL/lpr female mice. Administration of testosterone for 17 or 34 days dramatically reduced the extent of lymphocyte infiltration in lacrimal tissue: this hormone action was time-dependent and involved marked diminutions in both infiltrate size and area. Moreover, hormone therapy appeared to reverse the inflammation-induced disruption of acinar and ductal epithelium. Of interest, there was no significant difference in experimental results between the physiological and supraphysiological doses of testosterone. In contrast, the magnitude of lymphocyte infiltration progressively increased in lacrimal glands of placebo-treated mice during the experimental time course. Testosterone therapy also significantly diminished immunopathology in the submandibular gland, but the extent of this effect was less than found in lacrimal tissue.

EXAMPLE II

Androgen impact on lacrimal gland immunopathology in the NZB/NZW F1 mouse model of Sjögren's syndrome (48)

The objective of this investigation was to assess the efficacy of androgen treatment for lacrimal disease by utilizing another autoimmune, animal model (NZB/NZW F1 [F1] mouse) of Sjögren's syndrome (52,59). As in humans, lacrimal glands of this mouse strain, which displays a fundamental B cell defect, harbor dense, lymphocytic aggregates (50,52), which contain a prevalence of B and helper T cells (58). Moreover, this murine disease is accompanied by focal destruction of acinar and ductal tissue and apparent ocular surface dryness (50,52). In contrast, immune dysfunction in the MLR/lpr model appears to have a different etiology and involves a basic, immunoregulatory disorder of T cells (47).

Autoimmune, female F1 mice were treated systemically with vehicle or varying concentrations of testosterone for 0, 17, 34 or 51 days after the onset of disease; again, the systemic route for hormone treatment was utilized because lacrimal tissue in F1 mice may not be accessed from the ocular surface. Results showed that the extent of lymphocyte infiltration increased dramatically in control mice during the experimental time course. However, testosterone administration induced a significant, time-dependent decrease in lymphocytic accumulation in the lacrimal gland. Following 34 to 51 days of androgen therapy, the magnitude of lymphocyte infiltration had been suppressed 22- to 46-fold, compared to that in placebo-treated tissue. This hormone effect was associated with significant reductions in the number of focal infiltrates, the area of individual foci and the total quantity of lymphocyte infiltration per lacrimal section. In certain groups, testosterone exposure also stimulated a rise in tear volumes, relative to those measured in the same mice prior to treatment. With few exceptions, the impact of physiological and supraphysiological testosterone treatment on lacrimal autoimmune expression in F1 mice was essentially identical, the suppression of autoimmune disease.

EXAMPLE III

Effect of androgen therapy in Sjögren's syndrome: hormonal influence on lymphocyte populations and Ia expression in lacrimal glands of MRL/lpr mice Previous research demonstrated that androgen treatment dramatically curtails lymphocyte infiltration in lacrimal glands of mouse models of Sjögren's syndrome. The purpose of this study was to determine whether this androgen action involves the selective suppression of specific lymphocyte populations or Class II antigen (i.e., Ia) expression in lacrimal tissue. Towards this end, autoimmune female MRL/Mp-lpr/lpr mice were administered placebo- or testosterone-containing compounds systemically for 0, 17 or 34 days after the onset of disease. Results showed that androgen exposure exerts both a quantitative and a qualitative influence on inflammatory cell populations in the lacrimal gland of MRL/lpr mice. Thus, testosterone, but not placebo, treatment induced a precipitous decrease in the total number of T cells, helper T cells, suppressor/cytotoxic T cells, Ia-positive lymphocytes and B cells. Androgen administration also significantly diminished the lacrimal density, as well as the frequency, of B220$^+$ (i.e., possibly immature T) cells.

These findings, when compared with other observations (45,47, 48,56), suggest that testosterone's anti-inflammatoryactivity may be unique and lacrimal gland-specific. First, the androgen-induced immunosuppression in lacrimal tissue does not extend to peripheral lymph nodes (56,57), indicating that this steroid hormone does not cause a generalized depression in lymphocyte migration to, or proliferation in, systemicor mucosal sites. Second, testosterone exposure reduces the magnitude of lymphocytic infiltration in submandibular glands of MRL/lpr mice (47), but the nature of this hormonal influence may be unlike that found in lacrimal tissue, and the overall susceptibility of salivary focal infiltrates to androgens and pharmacological agents appears quite different from that found in lacrimal tissue (47). Third, androgens exert significant control over immunological functions in lacrimal glands, but not necessarily those of salivary or systemic tissues (45).

EXAMPLE IV

Impact of steroids and immunosuppressive agents on lacrimal autoimmune disease in the MRL/lpr mouse model of Sjögren's syndrome The objective of the following experiments was to determine whether other steroid hormones or immunosuppressive agents might duplicate the effect of testosterone on lacrimal gland autoimmunity. Female MRL/lpr mice were treated with systemic vehicle, steroids or immunosuppressive compounds for 21 days after disease onset. The pharmaceutical agents evaluated in this study included: (a) testosterone, which, has been shown to significantly reduce lacrimal gland inflammation; (b) 19-nortestosterone, an anabolic androgen with attenuated virilizing activity; (c) danazol, a synthetic steroid, which is utilized in the treatment of certain immune diseases in humans (81) and is known to diminish specific, peripheral immune defects in MRL/lpr mice (60); (d) 17β-estradiol, a female sex steroid, which has been hypothesized as a potential treatment for ocular disease in Sjögren's syndrome (4); (e) a synthetic, non-androgenic steroid, which apparently suppresses lymphocyte infiltration in salivary glands of F1 mice and corrects other systemic autoimmune defects; (f) cyclosporine A, an anti-inflammatory agent, which ameliorates specific, peripheral immune dysfunctions in MRL/lpr mice (61) and has been proposed as an effective therapeutic agent for lacrimal disease and KCS in Sjögren's syndrome (6); (g) dexamethasone, a potent anti-inflammatory glucocorticoid, that has been suggested as a possible therapeutic agent for lacrimal immunopathology in Sjögren's syndrome (26); and (h) cyclophosphamide, an immunosuppressive agent, that decreases various autoimmune sequelae in systemic (83–85) and salivary (59,82) sites in MRL/lpr mice. The comparative results demonstrated that the suppressive influence of testosterone on focal infiltrate area, number of foci and percentage lymphocyte infiltration in lacrimal tissue was duplicated by the administration of the anabolic androgen, 19-nortestosterone, or cyclophosphamide, but not by therapy with estradiol, danazol, the synthetic non-androgenic steroid, cyclosporine A, or dexamethasone. In addition, testosterone, 19-nortestosterone and cyclophosphamide, as well as dexamethasone, reduced lymphocyte infiltration in the submandibular gland. However, neither androgen interfered with the pronounced inflammation of lymphatic tissues, including the spleen, and superior cervical and mesenteric lymph nodes. Androgen treatment alone also stimulated an increase in the lacrimal gland output of total protein and IgA antibodies into tears; these antibodies, which protect the ocular surface against bacterial colonization, viral attachment, parasitic infestation and fungal- or toxin-induced impairment (46), are typically diminished in mucosal sites in Sjögren's syndrome (53).

Overall, these combined findings demonstrate that androgens, or their anabolic analogues, suppress autoimmune expression in, and enhance tissue function of, lacrimal glands of animal models of Sjögren's syndrome. Androgen action also appears to represent a tissue-specific response independent of generalized, systemic effects, thus justifying topical ocular therapeutic application. Cyclophosphamide, the only non-androgen to reduce lymphocyte infiltration in lacrimal tissue upon systemic administration, is not believed to be appropriate for topical therapy in humans because of its mode of action. This alkylating agent, which is thought to suppress autoimmune function by a direct modification of cellular DNA, must first be metabolized by the liver before becoming active. Therefore, cyclophosphamide would not be capable of local action upon topical application.

Local ocular application of TGF-β can relieve the immunopathology of Sjögren's syndrome The androgen-induced suppression of immunopathological lesions in autoimmune lacrimal tissue, and the parallel improvement in glandular function, could be mediated through an androgen interaction with epithelial cells, which would then cause the altered expression and/or activity of epithelial cytokines in the lacrimal gland. If correct, this hypothesis would predict that: (a) epithelial cells are the target cells for androgen action in the lacrimal gland, and that androgen receptors are located within epithelial, but not other (e.g., lymphocytic), cells in lacrimal tissue; and (b) androgens increase the expression of anti-inflammatory cytokines, or decrease the activity of pro-inflammatory peptides, in the lacrimal gland. Therefore, to address this hypothesis, experiments were conducted to identify the presence, location and/or cellular distribution of androgen receptor protein and mRNA in lacrimal glands of various species and autoimmune, female MRL/lpr mice, as well as examine the impact of androgens on cytokine levels in lacrimal tissue.

EXAMPLE 5

Presence, location and hormonal regulation of androgen receptors in lacrimal tissue The mechanism(s) by which androgens regulate the immune expression in the lacrimal gland undoubtedly involves an initial hormone association with specific androgen receptors. Androgen receptors appear to mediate almost all known activities of androgens and are members of the steroid/thyroid hormone/retinoic acid family of ligand-activated transcription factors (90–96). The location of androgen receptors in other tissues is predominantly intranuclear (97–99), due to the presence of a nuclear targeting signal, homologous to that of the SV 40 large T antigen, which occurs in the receptor hinge region immediately following the DNA-binding domain (93). Following androgen binding to the receptor, the monomeric, activated hormone-receptor complex associates with an androgen response element in the control region of specific target genes, typically dimerizes with another androgen-bound complex and, in combination with appropriate silencers, tissue-specific and basal promoter elements, regulates gene transcription (90,91,93,94,96). This androgen activity results in the alteration of mRNA production and ultimately protein synthesis in a variety of tissues (100–103); such regulation of protein elaboration appears to be the primary action of androgens (90,104).

A critical prerequisite, though, for the androgen-induced regulation of target gene transcription is the presence and location of androgen receptors in a given tissue (90). In fact, considerable research has demonstrated that a tissue's physiological responsiveness to steroids (e.g., androgens) is most often directly proportional to the concentration of that steroid's receptor protein, as well as to the amount of its associated mRNA (90,105,106).

Therefore, to determine whether high affinity and specific androgen receptors are present in the lacrimal gland, equilibrium binding methods were employed with various tritiated steroids and with lacrimal tissue cytosol from young adult, orchiectomized or ovariectomized rats. Analysis revealed that a single class of saturable, high-affinity and specific binding sites exist for androgens in lacrimal tissues of both male and female rats. To extend these findings, experiments were also performed to evaluate whether high-affinity androgen binding sites are located specifically within acinar epithelial cells of the rat lacrimal gland. Towards that end, acinar epithelial cells were isolated from lacrimal tissues of orchiectomized rats, processed for the preparation of cytosol and examined for tritiated dihydrotestosterone (DHT) binding sites. This analysis identified the existence of high-affinity androgen receptors within these cells.

To determine whether androgen receptor mRNA is present in lacrimal tissues of various species, the following studies were conducted. RNA was isolated from lacrimal glands of male and/or female mice, rats, hamsters, guinea pig, rabbits and human, as well as from rat spleen (negative control), rat prostate and human prostate LNCaP cells (positive controls), then reverse transcribed into cDNA, amplified with specific primers by polymerase chain reaction (PCR) and processed for Southern blot hybridization with a 32P-labeled fragment of rat androgen receptor cDNA. The size of amplified cDNA products was calculated by comparison to a series of molecular weight standards run in adjacent lanes in the 1.5% agarose gel. The results showed that lacrimal glands from all tested species contained a single, ~1,273 bp band of androgen receptor mRNA, which was identical to that observed in rat prostatic tissue and human prostatic LNCaP cells. In addition, the same RT-PCR results were found if "human-specific" oligomeric primers were utilized to amplify mRNA from human lacrimal tissue, LNCaP cells and rat prostate.

For comparative purposes, studies were also conducted to examine human and/or rat lacrimal glands for the existence of androgen receptor mRNA by the use of ribonuclease protection assays, as well as Northern blot techniques. In the former experiments, total cellular RNA was isolated from human lacrimal gland autopsy specimens (n=5 males, 1 female), LNCaP cells, as well as rat lacrimal, prostatic and splenic tissues, then hybridized to 32P-labeled, human or rat androgen receptor riboprobes. Findings showed that androgen receptor mRNA occurred in both human and rat lacrimal glands, and that the size was equivalent to that of the prostatic androgen receptor mRNA. In the ribonuclease protection assays with rat tissues, no androgen receptor mRNA was detected in the spleen, whereas G-3-PDH mRNA was evident in all rat lacrimal, prostatic and splenic samples. For comparison, it has also been demonstrated that androgen receptor mRNA occurs in rat lacrimal tissue, and that the molecular size (~10 kb; by Northern blots) is identical to that observed in the prostate, an androgen target organ (107).

To explore the endocrine basis for the androgen regulation of both the structure and function of the lacrimal gland in a variety of species, studies were also designed to: (a) determine the cellular distribution of androgen receptors in the lacrimal gland; and (b) examine the influence of gender and the endocrine environment on the glandular content of these binding sites. Lacrimal glands were obtained from intact, castrated, or sham-operated male or female adult rats, mice or hamsters, as well as from orchiectomized rats exposed to placebo compounds or physiological levels of testosterone. The cellular location of androgen receptors was evaluated by utilizing an immunoperoxidase protocol, in which a purified rabbit polyclonal antibody to the rat androgen receptor was used as the first antibody. Findings with lacrimal glands showed that: (a) androgen receptors are located almost exclusively in nuclei of epithelial cells; (b) the cellular distribution or intranuclear density of these binding sites is far more extensive in glands of males, as compared to females; (c) orchiectomy, but not sham-surgery, leads to a dramatic reduction in the immunocytochemical expression of androgen receptors; and (d) testosterone administration to orchiectomized rats induces a marked increase in androgen receptor content, relative to that in placebo-exposed glands. Overall, these findings demonstrate that gender and the endocrine system may significantly influence the distribution of androgen binding sites in rat lacrimal tissue. Moreover, these results show that androgens up-regulate their own lacrimal gland receptors.

To assess whether the androgen control of, and gender-related differences in, androgen receptor protein in the lacrimal gland are associated with variations in the expression of androgen receptor mRNA, the following study was performed. Orchiectomized and ovariectomized Sprague-Dawley rats were administered subcutaneous implants of placebo- or testosterone-containing pellets for 7 days. Lacrimal glands were obtained from these animals, as well as intact male, female and sham-operated rats, and then processed for the measurement of androgen receptor mRNA by semi-quantitative reverse transcription (RT)-PCR. All androgen receptor mRNA determinations were standardized to the $\beta$-actin content in the same RNA sample. The results of this study showed that the levels of androgen receptor mRNA are significantly higher in lacrimal tissues of females, as compared to males. In addition, the findings demonstrated that orchiectomy increases, and androgen treatment reduces, androgen receptor mRNA content in lacrimal tissue. Thus, the effects of gender and androgen exposure on AR mRNA expression in the lacrimal gland are the opposite to those observed with AR protein. This type of AR autoregulation has also been found by other investigators in certain reproductive tissues.

The above findings demonstrate that androgen receptor protein and mRNA are present in lacrimal tissues of a number of species and that these binding sites possess high affinity, are specific for androgens, and are located almost entirely within nuclei of epithelial cells. To extend these results further, additional studies were performed to identify the cellular target(s) within autoimmune lacrimal tissue that may mediate the immunosuppressive effect of androgens. In addition, the endocrine regulation of androgen receptors in these autoimmune lacrimal glands was explored. Adult, female MRL/lpr mice were exposed systemically to vehicle, steroid hormones or immunosuppressive agents for varying time intervals after the onset of disease. Immediately before or after treatment, lacrimal glands were obtained and processed to determine the cellular distribution and nuclear density of androgen receptors by immunoperoxidase and image analysis techniques, and to assess the levels of androgen receptor mRNA. The findings demonstrated that: (a) androgen receptors exist almost exclusively within nuclei of acinar and ductal epithelial cells in lacrimal tissue of MRL/lpr mice; (b) androgen receptors are not detectable in the extensive lymphocytic populations that infiltrate the gland; (c) testosterone administration induces a significant increase in the number of androgen receptor-containing cells in, as well as the density of androgen receptors in epithelial cell nuclei of, lacrimal tissue; (d) hormone action is steroid-specific: administration of androgen analogues, but not estrogens, glucocorticoids or cyclophosphamide, stimulate the accumulation of androgen receptors; (e) androgens autoregulate the amount of their receptor mRNA; and (f) androgen receptor density is significantly reduced following the withdrawal of androgen therapy. These results show that epithelial cells, but not lymphocytes, are the androgen target cells in lacrimal tissue, and appear to mediate the androgen-related immunosuppression and functional enhancement in lacrimal glands of autoimmune female mice. These findings also demonstrate that androgens increase the expression of their own receptor protein, and decrease the content of their receptor mRNA, in MRL/lpr lacrimal tissue.

In summary, these results show that epithelial cells, but not lymphocytes, are the androgen target cells in autoimmune lacrimal tissues, and that androgens up-regulate the expression of their own receptor protein in these cells. In addition, it has been shown that: (a) specific, high-affinity and saturable androgen binding sites exist in rat lacrimal tissue; (b) the location of these receptors is almost exclusively within epithelial cells of lacrimal glands in non-autoimmune mice, rats and hamsters; (c) androgen receptor mR/gA is present in lacrimal tissues of humans and numerous other species; (d) the appearance of androgen receptor protein and mRNA in the lacrimal gland is significantly influenced by gender and androgens; and (e) androgen act directly on epithelial cells of the rat lacrimal gland and these hormone actions may be inhibited by cellular exposure to androgen receptor, transcription and translation antagonists (108,109).

EXAMPLE 6

Role of epithelial cell TGF-β in lacrimal gland autoimmune disease

Autoimmune diseases invariably involve a deficiency in self tolerance, the generation of autoreactive immune cells, the activation of proto-oncogenes and the expression of immune response genes to the detriment of the host (110–112). However, an additional and extremely important feature of autoimmune disorders is the inappropriate secretion of cytokines (111,112). These peptides, which are produced by a wide variety of cells, e.g., immune, epithelial, endothelial, and neural (112–116), have been termed the "hormones of the immune system" (117) and normally play an integral role in immunological defense (112,118). An imbalanced production and release of cytokines, though, may lead to the subversion of tolerance to specific antigens, activation of effector functions of T and B cells, stimulation of proto-oncogene, Class II antigen and intercellular adhesion molecule expression, promotion of the inflammatory process and destruction of target cells, e.g., epithelial (110, 112,117–120). Given these actions, cytokines have also been implicated as the "mediators of autoimmune disease" (121). At present, numerous cytokines appear to be involved in autoimmune disorders (111,112,117–119,122) and to contribute significantly to the etiology and/or generation of inflammatory eye diseases (123,124).

Recently, studies have also implicated cytokines in the development and perpetuation of severe immunopathological lesions in exocrine tissues of Sjögren's syndrome patients (125), as well as in the striking decrease in glandular secretion that occurs in this disorder (126). Thus, salivary glands of individuals with Sjögren's syndrome show a tremendous increase in the interleukin-1 (IL-1), IL-6 and tumor necrosis factor-α (TNF-α) mRNA levels in acinar epithelial cells, a substantial rise in IL-2, IL-10 and IFN- mRNA content in CD4 T cells, and a significant elevation in IL-1, IL-6, TNF-α, IL-10 and IFN- concentrations in saliva, relative to those amounts in healthy controls (127). Analyses of total salivary gland biopsies have also documented alterations in the mRNA expression of these cytokines, as well as of IL-1β and TGF-β mRNA (128–130). With regard to lacrimal glands, a limited evaluation of biopsies from Sjögren's syndrome patients by RT-PCR has identified elevated amounts of IL-1β, IL-6 and IFN- mRNA (128,131). Of interest, these changes in cytokine circuitry might explain not only the inflammatory progression of this disease, but also the associated xerophthalmia and xerostomia in Sjögren's syndrome. Thus, cytokine-induced lymphocyte infiltration may result in a significant decline in the neural innervation of inflamed tissue (132). Moreover, certain cytokines (e.g., IL-1β) may directly suppress transmitter release by adrenergic and cholinergic nerves (133), thereby interfering with the neural control of epithelial cell fluid secretion (126).

This aberrant expression of cytokines in Sjögren's syndrome may well be due, in part, to the influence of sex steroids. In support of this hypothesis, estrogens, which may be involved in the pathogenesis, acceleration and amplification of Sjögren's syndrome (30,31), are known to enhance the production of pro-inflammatory cytokines, e.g., IL-1 and TNF-α (134). Conversely, androgens, which decrease the manifestations of many autoimmune disorders (16,37,135), may elicit the generation of immunosuppressive cytokines (136). In fact, the sex steroid regulation of cytokine synthesis is believed to account for the distinct sexual dimorphism found in the incidence of autoimmune disease (122).

Indeed, the principle mechanism by which androgens suppress autoimmune disease in lacrimal glands of female mouse models of Sjögren's syndrome may well be through the control of epithelial cell cytokine production. In support of this hypothesis, as has been described above, the anti-inflammatoryaction of androgens in lacrimal tissue appears to be mediated not through lymphocytes, but rather through epithelial cells. Moreover, epithelial cells in other tissues are known to secrete numerous cytokines, e.g., TGF-β (137), and also serve in exocrine sites as active cellular participants in the glandular inflammation in Sjögren's syndrome (138). In addition, as will be described below, androgens increase the mRNA and protein levels of the immunosuppressive cytokine, TGF-β1, in the lacrimal gland. This cytokine is thought to play a protective role in Sjögren's syndrome, and increased expression of TGF-β mRNA has been correlated with reduced inflammation in salivary glands of Sjögren's syndrome patients (129). In contrast, the absence of TGF-β1 leads to a pronounced lymphocytic infiltration into both lacrimal and salivary glands (139).

Therefore, to test this hypothesis, studies were performed identify epithelial cell cytokines that may mediate, or be involved, in the androgen-induced suppression of lacrimal gland inflammation in Sjögren's syndrome. An initial inquiry was whether lacrimal gland epithelial cells express cytokines, that might be involved in the endocrine regulation of immune function in this tissue. These studies, which were conducted with high stringency, RT-PCR procedures, demonstrated that TGF-β1, TGF-β2, TGF-β3, IL-6, TNF-α and IL-1α mRNA may be detected consistently in lacrimal glands, as well as in isolated lacrimal acinar epithelial cells, of male and female rats. As a corollary to these studies, whether lacrimal glands of autoimmune mice contain mRNAs for anti-inflammatory, as well as pro-inflammatory, cytokines was also examined. This research, which was performed with high stringency RT-PCR techniques, showed that mRNA for IL-1α, IL-1β, IL-2 receptor, IL-6, TGF-β and TNF-α may be detected consistently in lacrimal glands of autoimmune female MRL/lpr mice. The identity of these amplified products was verified by agarose gel electrophoresis, molecular weight determinations and comparison to several positive controls (e.g., cDNA from MRL/lpr splenic tissue, P388D1 macrophages, and Clontech kit controls).

Given these findings, the next set of studies was designed to determine whether the mRNA and protein levels of the immunoinhibitory cytokine, TGF-β1, in the lacrimal gland might be controlled by androgens, and influenced by gender. In the first series of experiments, total RNA was isolated from lacrimal glands of intact, castrated or sham operated male and female rats, as well as placebo- or testosterone-treated orchiectomized rats. Following this isolation, TGF-β1 and β-actin mRNA were analyzed by agarose gel electrophoresis, RT-PCR, Southern hybridization, autoradiography and densitometry. For control purposes, all TGF-β1 measurements were standardized to those of β-actin. The results demonstrated that: (a) levels of TGF-β1 mRNA were significantly higher in lacrimal tissues of intact male, as compared to those of female, rats; (b) orchiectomy either decreased, or had no impact, on TGF-β1 mRNA content in lacrimal glands, whereas ovariectomy consistently had no effect on TGF-β1 mRNA amounts; and (c) androgen treatment significantly increased TGF-β1 mRNA expression in lacrimal tissues of orchiectomized rats, relative to that in glands of placebo-treated controls. These data demonstrated that gender influences, and androgens regulate, TGF-β1 mRNA levels in the lacrimal gland.

A second series of studies examined whether androgen exposure might significantly increase the content of TGF-β1 protein in lacrimal tissues of autoimmune mice. Accordingly, lacrimal tissues were obtained from female MRL/lpr mice after the onset of disease and following placebo, testosterone or cyclophosphamide treatment. Glands were then processed for the acid extraction of proteins and the analysis of TGF-β1 levels by use of a commercial assay. The results showed that androgen, but not cyclophosphamide, administration stimulated a significant rise in the total amount of TGF-β1 protein in lacrimal tissues of female MRL/lpr mice, as compared to levels in tissues of placebo controls.

Overall, these findings show that the mRNAs for cytokines believed to play a major role in exocrine tissue inflammation in Sjögren's syndrome are present in lacrimal tissues of normal rats and autoimmune mice. In addition, these results demonstrate that androgens stimulate the accumulation of TGF-β1 mRNA and protein in the lacrimal gland. TGF-β1, in turn, is known to exert profound immunosuppressive activity, including the inhibition of T and B cell proliferation, cytotoxic T cell generation, natural and lymphokine-activated killing, T cell adhesion to the endothelium, macrophage function and IL-1, TNF and IFN-g production, and is believed to down regulate inflammation in exocrine glands in Sjögren's syndrome (129,139, 140). Consequently, the androgen-induced increase in TGF-β1 could act to suppress lymphocytic infiltration and to attenuate IL-1 and TNF-α production in the lacrimal gland. These hormonal effects would then provide a mechanistic explanation for the androgen-related suppression of autoimmune disease in lacrimal tissue during Sjögren's syndrome.

As an additional consideration, it is important to note that the androgen-induced rise in TGF-β content in the lacrimal gland will undoubtedly lead to enhanced secretion of TGF-β by lacrimal tissue and to an increased concentration of TGF-β in tears. Given that TGF-β (e.g., TGF-β1, TGF-β2) has been detected in tears, measurement of this latter androgen-associated effect in tears, by utilization of commercial or conventionally-prepared assay kits, would serve as an ideal diagnostic test to monitor the efficacy of topically applied androgens for the treatment of dry eye.

USE

Topical application of androgens or their analogues to patients with Sjögren's syndrome or other autoimmune diseases of the lacrimal gland can directly suppress the immunopathological defects in accessory lacrimal tissue and the main lacrimal gland's palpebral lobe, which is adjacent to the ocular surface. Selection of the most appropriate therapeutic compounds will depend upon a given hormone's immunological activity, potential side effects and form of administration. For example, topical testosterone may be quite effective in reducing lacrimal inflammation, and its methylated analogue appears to have no toxic side effects on parameters such as intraocular pressure (87). However, utilization of testosterone as a pharmaceutical agent may be contraindicated: this hormone's metabolism, in various peripheral tissues, may involve aromatization to estrogens (86), which may exacerbate the ongoing autoimmune disease. In addition, with regards to administration, if the androgen is to be complexed to a carrier vehicle (e.g., hyaluronate), then a nitrogenated analogue might be indicated.

Therefore, the efficacy of a variety of modified and/or anabolic androgens in suppressing lacrimal gland autoimmune expression in female MRL/lpr mice was compared. Animals were administered vehicle or designated androgens systemically for 6 weeks after the onset of disease. The androgens examined in this test included: (a) testosterone; (b) dihydrotestosterone (also termed allodihydrotestosterone, androstanolone, stanolone, 5α-dihydrostestosterone); (c) fluoxymesterone; (d) stanozolol; (e) nortestosterone propionate; (f) dehydroepiandrosterone (an androgen precursor, also termed androstenolone, dehydroisoandrosterone, DHEA, transdehydroandrosterone); (g) oxandrolone; (h) methyldihydrotestosterone (also termed methylandrostanolone); (i) orymetholone; (j) 5α-androstan-17β-ol-3-oxime; (k) 5α-androstan-17α-ol-3-one-acetate; (l) 2, (5α)-androsten-17β-ol; (m) 5α-androstan-2α-methyl-17β-ol-3-one; and (n) methyl testosterone.

The rationale for comparing the immunological activity of this specific array of androgenic compounds was multifold:

First, these hormones are representative of the major structural subclasses of androgens, as disclosed in Vida (88), hereby incorporated by reference. The subclasses include (a) androgenic compounds with unusual structural features (e.g., 17α-methyl-17β-hydroxy-2-oxa-5α-androstan-3-one, also termed oxandrolone); (b) testosterone derivatives (e.g., methyltestosterone); (c) 4,5α-dihydrotestosterone derivatives (oxymetholone); (d) 17β-hydroxy-5α-androstane derivatives containing a ring A unsaturation, excluding testosterone derivatives (e.g., 2,(5α)-androsten-17β-ol); and (e) 19-nortestosterone derivatives (e.g., 19-nortestosterone propionate). It may be that certain structural features impart more optimal immunosuppressive characteristics, which would be of benefit in selecting specific androgens for human use.

Second, relative to standards (typically testosterone), these androgens include compounds displaying: (a) augmented androgenic (i.e., virilizing) activity coupled with an even larger increase in anabolic activity (e.g., fluoxymesterone); (b) enhanced anabolic action with unchanged androgenic effects (e.g., oxymetholone, dihydrotestosterone); (c) decreased androgenic ability with unchanged anabolic activity (e.g., 19-nortestosterone propionate); and (d) decreased androgenic capacity paralleled by increased anabolic activity (e.g., oxandrolone, stanozolol). Thus, the analysis should identify an androgen with far more anabolic, than virilizing, activity to be utilized for the treatment of ocular manifestations of Sjögren's syndrome (e.g., oxandrolone possesses 322% of the anabolic and 24% of the androgenic activity of methyltestosterone (88)). Of course, it is possible that anabolic effects, per se, may not be involved in androgen suppression of lacrimal autoimmune symptoms. However, the results with 19-nortestosterone in MRL/lpr mice demonstrate that this anabolic androgen, which has significantly reduced androgenic activity in lacrimal tissue (89), was equally as effective as testosterone in abrogating lymphocyte infiltration in the lacrimal gland.

Third, these compounds contain a nitrogen-substituted androgen, 5α-androstan-17β-ol 3-oxime, which is created by the substitution of a nitrogen derivative for the 3-ketone function in dihydrotestosterone (very potent androgen) (88). This substitution does not inhibit androgen activity (88) and may permit steroid binding to hyaluronate for topical administration. Of interest, a variety of other nitrogenated androgens have been shown to express increased anabolic, but decreased androgenic, activity. These compounds typically contain 3-substitutions, but not nitrogen incorporation in the steroid ring structure, which appears to abolish androgen action (88).

The results of testing the effect of the representative compounds were that all androgen classes, whether parental, modified or anabolic analogue, were effective in suppressing lacrimal gland autoimmune expression, although to various degrees. With further routine additional testing, the most appropriate therapeutic compound for a specific application can be determined.

Androgen therapy, which can be administered in the form of drops (e.g., free hormone, or complexed with carrier substances, such as hyaluronate) or ointment, should not require frequent applications, considering the mechanism and duration of androgen/cell interactions. The administration of a specific compound would be by routine methods in pharmaceutically acceptable substances, including buffer solutions (e.g., phosphate buffered saline) or inert carrier compounds, to the ocular surface or adjacent regions of the eye. Optimal dosage and modes of administration can readily be determined by conventional protocols. This treatment can: (a) decrease lymphocyte infiltration in adjacent lacrimal tissue and thereby alleviate immune-mediated destruction, and lymphocyte compression, of acinar and ductal cells; (b) permit accessory and/or palpebral lacrimal glands to secrete basal tear volumes; it is estimated that a tear secretion rate of only 0.1 μl/minute (i.e., one-tenth of normal) could maintain a stable tear film under favorable conditions (1); and (c) make available regions of functional lacrimal tissue, that might respond to exogenous tear stimulants to enhance surface volume.

Topical administration of androgens would avoid the numerous side effects of parallel systemic exposure to these hormones, including virilization, menstrual irregularities (e.g. amenorrhea), hepatic dysfunction, edema, hematologic abnormalities, behavioral changes and metabolic alterations. In addition, the therapeutic augmentation of basal tear secretion could allow the use of visual aids, such as contact lenses, in the Sjögren's syndrome or other autoimmune patient population.

TGF-β therapy can be administered in the form of drops or locally by injection. The administration of a specific compound would be by routine methods in pharmaceutically acceptable substances including buffer solutions (e.g., phosphate buffered saline) or inert carrier compounds, to the ocular surface or adjacent regions of the eye. The dosage of TGF-β administered (preferably in the range of 10 pg to 10 mg, and more preferably 10 ng to 10 μg) can be optimized according to the formulation and method of delivery, and the mode of administration can be readily determined by conventional protocols. This TGF-β treatment should suppress lymphocyte infiltration in adjacent lacrimal tissue and thereby ameliorate immune-mediated destruction of acinar and ductal epithelial cells.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

References

1. Holly, F. J., Tear film physiology. Internat. Ophthalmol. Clin. 27:2–6 (1987).
2. Whitcher, J. P., Clinical diagnosis of the dry eye. Internat. Ophthalmol. Clin. 27:7–24 (1987).
3. Lamberts, D. W., Keratoconjunctivitis sicca. In "The Cornea. Scientific Foundations and Clinical Practice" (G. Smolin, and R. A. Thoft, Eds.), pp. 293–308, Little, Brown and Co, Boston, Mass. (1983).
4. Lemp, M. A., Recent developments in dry eye management. Ophthalmology 94:1299–1304 (1987).
5. Lubniewski, A. J., and Nelson, J. D., Diagnosis and management of dry eye and ocular surface disorders. Ophthalmol. Clin. N. A. 3:575–594 (1990).
6. Kaswan, R., Cyclosporine drops: a potential breakthrough for dry eye. Res. Prey. Blindness Writers Seminar, pp. 18–20 (1989).
7. Tabbara, K. F., Sjögren's Syndrome In "The Cornea. Scientific Foundations and Clinical Practice" (G. Smolin, and R. A. Thoft, Eds.), pp. 309–314, Little, Brown and Co, Boston, Mass. (1983).
8. Moutsopoulos, H. M., and Talal, N., Immunologic abnormalities in Sjögren's syndrome. In "Sjögren's Syndrome. Clinical and Immunological Aspects" (N. Talal, H. M. Moutsopoulos, and S. S. Kassan, Eds.), pp. 258–265, Springer Verlag, Berlin (1987).
9. Talal, N., and Moutsopoulos, H. M., Treatment of Sjögren's syndrome. In "Sjögren's Syndrome. Clinical and Immunological Aspects" (N. Talal, H. M. Moutsopoulos, and S. S. Kassan, Eds.), pp. 291–295, Springer Verlag, Berlin (1987).
10. Kincaid, M. C., The eye in Sjögren's syndrome. In "Sjögren's Syndrome. Clinical and Immunological Aspects" (N. Talal, H. M. Moutsopoulos, and S. S. Kassan, Eds.), pp. 25–33, Springer Verlag, Berlin (1987).
11. Daniels, T. E., and Talal, N., Diagnosis and differential diagnosis of Sjögren's syndrome. In "Sjögren's Syndrome. Clinical and Immunological Aspects" (N. Talal, H. M. Moutsopoulos, and S. S. Kassan, Eds.), pp. 193–199, Springer Verlag, Berlin (1987).
12. Daniels, T. T., Aufdemorte, T. B., and Greenspan, J. S., Histopatholoy of Sjögren's syndrome. In "Sjögren's Syndrome. Clinical and Immunological Aspects" (N. Talal, H. M. Moutsopoulos, and S. S. Kassan, Eds.), pp. 41–52, Springer Verlag, Berlin (1987).
13. Alexander, E. L., Neuromuscular complications of primary Sjögren's syndrome. In "Sjögren's Syndrome. Clinical and Immunological Aspects" (N. Talal, H. M. Moutsopoulos, and S. S. Kassan, Eds.), pp. 61–82, Springer Verlag, Berlin (1987).
14. Daniels, T. E., Sjögren's syndrome—in a nut shell. Sjögren's Syndrome Foundation Inc. Report, Port Washington, N.Y. (1990).

15. Talal, N., and Ansar Ahmed, S., Sex hormones and autoimmune disease: a short review. Int. J. Immunotherapy 3:65–70 (1987).
16. Ansar Ahmed, S., Penhale, W. J., and Talal, N., Sex hormones, immune responses and autoimmune diseases. Am. J. Pathol. 121:531–551 (1985).
17. Burns, J. C., Persistent cytomegalovirus infection. The etiology of Sjögren's syndrome. Med. Hypotheses 10:451–460 (1983).
18. Fox, R. I., Pearson, G., and Vaughan, J. H., Detection of Epstein-Barr virus-associated antigens and DNA in salivary gland biopsies from patients with Sjögren's syndrome. J. Immunol. 137:3162–3168 (1986).
19. Pflugfelder, S. C., Tseng, S. C. G., Pepose, J. S., Fletcher, M. A., Klimas, N., and Feuer, W., Epstein-Barr virus infection and immunological dysfunction in patients with aqueous tear deficiency. Ophthalmology 97:313–323 (1990).
20. Pepose, J. S., Akata, R. F., Pflugfelder, S. C., and Voigt, W., Mononuclear cell phenotypes and immunoglobulin gene rearrangements in lacrimal gland biopsies from patients with Sjögren's syndrome. Ophthalmology 97:1599–1605 (1990).
21. Green, J. E., Hinrichs, S. H., Vogel, J., and Jay, G., Exocrinopathy resembling Sjögren's syndrome in HTLV-1 tax transgenic mice. Nature 341:72–74(?).
22. Garry, R. F., Fermin, C. D., Hart, D. J., Alexander S. S., Donebower, L. A., and Luo-Zhang, H., Detection of a human intracisternal A-type retroviral particle antigenically related to HIV. Science 250:1127–1129 (1990).
23. Fox, R., Epstein-Barr virus and human autoimmune diseases: possibilities and pitfalls. J. Vir. Meth. 21:19–27 (1988).
24. Maini, R. N., The relationship of Sjögren's syndrome to Rheumatoid Arthritis. In "Sjögren's Syndrome. Clinical and Immunological Aspects" (N. Talal, H. M. Moutsopoulos, and S. S. Kassan, Eds.), pp. 165–176, Springer Verlag, Berlin (1987).
25. Venables, P. J. W., Teo, C. G., Baboonian, C., Griffin, B. E., Hughes, R. A., and Maini, R. N., Persistence of Epstein-Barr virus in salivary gland biopsies from healthy individuals and patients with Sjögren's syndrome. Clin. Exp. Immunol. 75:359–364 (1989).
26. Tabbara, K. F., and Frayha, R. A., Alternate-day steroid therapy for patients with primary Sjögren's syndrome. Annals Ophthalmol. 15:358–361 (1983).
27. Prijot, E., Bazin, L., and Destexhe, B., Essai de traitment hormonal de la keratocon-jonctivite seche. Bull. Soc. Belge Ophtalmol. 162:795–800 (1972).
28. Drosos, A. A., Skopouli, F. N., Galanopoulou, K., Kitridou, R. C., and Moutsopoulos, H. M., Cyclosporin A therapy in patients with primary Sjögren's syndrome: results at one year. Scand. J. Rheum. Suppl. 61:246–249 (1986).
29. Nasu, M., Matsubara, O., and Yamamoto, H., Postmortem prevalence of lymphocytic infiltration of the lacrymal gland: a comparative study in autoimmune and non-autoimmune diseases. J. Pathology 143:11–15 (1984).
30. Carlsten, H., Tarkowski, A., Holmdahl, R., and Nilsson, L. A., Oestrogen is a potent disease accelerator in SLE-prone MRL lpr/lpr mice. Clin. Exp. Immunol. 80:467–473 (1990).
31. Ahmed, S. A., Aufdemorte, T. B., Chen, J. R., Montoya, A. I., Olive, d., and Talal, N., Estrogen induces the development of autoantibodies and promotes salivary gland lymphoid infiltrates in normal mice. J. Autoimmunity 2:543–552 (1989).
32. Frost-Larsen, K., Isager, H., and Manthorpe, R., Sjögren's syndrome treated with bromhexine: a randomized clinical study. Br. Med. J. 1:1579–1581 (1978).
33. Gilbard, J. P., Rossi, S. R., Heyda, K. G. and Dartt, D. A., Stimulation of tear secretion and treatment of dry-eye disease with 3-isobutyl-1-methylxanthine. Arch. Ophthalmol. 109:672–676 (1991).
34. Manthorpe, R., Petersen, S. H., and Prause, J. U., Mucosolvan in the treatment of patients with primary Sjögren's syndrome. Acta Ophthalmol. (Copenh) 62:537–541 (1984).
35. Kriegbaum, N. J., yon Linstow, M., Oxholm, P., and Prause, J. U., A follow-up study of the progress of keratoconjunctivitis sicca and response to treatment in primary Sjögren's syndrome. Scand. J. Rheumatol. 18:193–196 (1989).
36. Raveche, E. S., and Steinberg, A. D., Sex hormones in autoimmunity. In "Pituitary Function and Immunity" (I. Berczi, Ed.), pp. 283–301, CRC Press, Boca Raton, Fla. (1986).
37. Ahmed, S. A., and Talal, N., Sex hormones and the immune system-part 2. Animal data. Bailliere's Clin. Rheum. 4:13–31 (1990).
38. Roubinian, J. R., Talal, N., Greenspan, J. S., Goodman, J. R., and Siiteri, P. K., Effect of castration and sex-hormone treatment on survival, anti-nucleic acid antibodies, and glomerulonephritis in NZB/NZW F1 mice. J. Exp. Med. 147:1568–1583 (1978).
39. Melez, K. A., Boegel, W. A., and Steinberg, A. D., Therapeutic studies in New Zealand mice. VII. Successful androgen treatment of NZB/NZW F1 females of different ages. Arthritis Rheum. 23:41–47 (1980).
40. Nelson, J. L., and Steinberg A. D., Sex steroids, autoimmunity, and autoimmune diseases. In "Hormones and Immunity" (I. Berczi, and K. Kovacs, Eds.), pp. 93–119, MTP Press Limited, Lancaster, England (1987).
41. Shear, H. L., Wofsy, D. and Talal, N., Effects of castration and sex hormones on immune clearance and autoimmune disease in MRL/Mp-lpr/lpr and MRL/Mp-+/+ mice. Clin. Immunol. Immunopathol. 26:361–369 (1983).
42. Ansar Ahmed, S., Young, P. R., and Penhale, W. J., Beneficial effect of testosterone in the treatment of chronic autoimmune thyroidiris in rats. J. Immunol. 136:143–147 (1986).
43. Allen, J. B., Blatter, D., Calandrea, G. B., and Wilder, R. L., Sex hormonal effects on the severity of streptococcal cell wall induced polyarthritis in the rat. Arthritis Rheum. 26:560–565 (1983).
44. Ahn, Y. S., Harrington, W. J., Simon, S. R., Mylvagnam, R., Pall, L. M., and So, A. G., Danazol for the treatment of idiopathic thrombocytopenic purpura. N. Engl. J. Med. 308:1396–1399 (1983).
45. Sullivan, D. A., Hormonal influence on the secretory immune system of the eye. In "The Neuroendocrine-Immune Network" (I. Berczi, Ed.), pp. 199–238, CRC Press, Boca Raton, Fla., (1990).
46. MacDonald, T. T., Challacombe, S. J., Bland, P. W., Stokes, C. R., Heatley, R. V., McI Mowat, A., Eds, "Advances in Mucosal Immunology," pp. 1–948, Kluwer Academic Publishers, London, England (1990).
47. Ariga, H., Edwards, J., and Sullivan, D. A. Androgen control of autoimmune expression in lacrimal glands of MRL/Mp-lpr/lpr mice. Clinical Immunology and Immunopathology 53:499–508 (1989).
48. Vendramini, A. C, Soo, C. H., and Sullivan, D. A., Testosterone-induced suppression of autoimmune disease 49. Bizzarro, A., Valentini, G., Di Marinto, G., Daponte, A., De Bellis, A., and Iacono, G., Influence of testosterone therapy on clinical and immunological features of autoimmune diseases associated with Klinefelter's syndrome. J. Clin. End. Metab. 64:32–36 (1987).
50. Hoffman, R. W., Alspaugh, M. A., Waggle, K. S., Durham, J. B., and Walker, S. E., Sjögren's syndrome in MRL/1 and MRL/n mice. Arthritis Rheum. 27:157–165 (1984).
51. Jabs, D. A., Alexander, E. L., and Green, W. R., Ocular inflammation in autoimmune MRL/Mp mice. Invest. Ophthalmol. Vis. Sci. 26:1223–1229 (1985).
52. Kessler, H. S., A laboratory model for Sjögren's syndrome. Am. J. Pathol. 52:671–678 (1968).
53. Celenligil, H., Kansu, E., Ruacan, S., and Eratalay, K., Secretory immune system and mucosal immunohistology in Sjögren's syndrome. Adv. Exp. Biol. Med. 216B:1641–1648 (1987).
54. Drosos, A. A., Vliet-Dascalopoulou, E., Andonopoulos, A. P., Galanopoulou, V., Skopouli, F. N., and Moutsopoulos, H. M., Nandrolone decanoate (decadurabolin) in primary Sjögren's syndrome: a double blind study. Clin. Exp. Rheum. 6:53–57 (1988).
55. Hene, R. J., Kruize, A., Kater, L., Gmelig, F. H. J., and Oei, H. Y., Lack of clinical effect of the androgenic steroid nandrolone on primary Sjögren's syndrome (PSS). Clin. Exp. Rheum. 9:338 (1991).
56. Steinberg, A. D., Roths, J. B., Murphy, E. D., Steinberg, R. T., and Raveche, E. S., Effects of thymectomy or androgen administration upon the autoimmune disease of MRL/Mp-lpr/lpr mice. J. Immunol. 125:871–873 (1980).
57. Brick, J. E., Walker, S. E., and Wise, K. S., Hormone control of autoantibodies to calf thymus nuclear extract (CTE) and DNA in MRL-lpr and MRL-+/+ mice. Clin. Immunol. Immunopathol. 46:68–81 (1988).
58. Jabs, D A, and Prendergast, R A: Murine models of Sjögren's syndrome. Invest. Ophthalmol. Vis. Sci. 29:1437 (1988).
59. Jonsson, R. L., Tarkowski, A., Backman, K., and Klareskog, L., Immunohistochemical characterization of sialoadenitis in NZB x NZW F1 mice. Clin. Immunol. Immunopathol. 42:93–101 (1987).
60. Connolly, K. M., Stcher, V. J., Snyder, B. W., Bobnet, E., and Potts, G. O., The effect of danazol in the MRL/lpr mouse model of autoimmune disease. Agents Actions 25:164–170 (1988).
61. Mountz, J. D., Smith, H. R., Wilder, r. L., Reeves, J. P., and Steinberg, A. D., CS-A therapy in MRL-lpr/lpr mice: amelioration of immunopathology despite autoantibody production. J. Immunol. 138:157–163 (1987).
62. Hazelton, R. A., McCruden, A. B., Sturrock, R. D., and Stimson, W. H., Hormonal manipulation of the immune response in systemic lupus erythematosus: a drug trial of an anabolic steroid, 19-nortestosterone. Annals Rheum. Dis. 42:155–157 (1983).
63. Lahita, R., Sex hormones, Sjögren's syndrome and the immune response. The Moisture Seekers Newsletter 8:1 (1991).
64. Comsa, J., Leonhardt, H., and Wekerle, H., Hormonal Coordination of the immune response, Rev. Physiol. Biochem. Pharmacol. 92:115–191 (1982).
65. Grossman, C. J., Regulation of the immune system by sex steroids, Endocr. Rev., 5:435–455 (1984).
66. Munck, A., Guyre, P. M. and Holbrook, N. J., Physiological functions of glucocorticoids in stress and their relation to pharmacological actions, Endocr. Rev., 5:25–44 (1984).
67. Besedovsky, H. O., del Rey, A. E. and Sorkin, E., Immune-neuroendocrine interactions, J. Immunol., 135:750–754 (1985).
68. Berczi, I., Pituitary Function and Immunity, pp. 1–347, CRC Press, Boca Raton, Fla. (1986).
69. Berczi, I. and Kovacs, K., Hormones and Immunity, pp. 1–332, MTP Press, Ltd., Lancaster, England (1987).
70. Jancovik, B. D., Markovic, B. M., and Spector, N. H., Neuroimmune Interactions, Ann. N.Y. Acad. Sci. 496, New York Acad. Sci., New York (1987).
71. Weigent D. A., Blalock J., Interactions between the neuroendocrine and immune systems: common hormones and receptors. Immunol. Rev. 100:79–108 (1987).
72. Freier, S., Ed., "The Neuroendocrine-Immune Network", pp. 1–266, CRC Press, Boca Raton, Fla. (1990).
73. Hadden, J. W., Masek, K., Nistico, G., Eds., "Interactions Among Central Nervous System, Neuroendocrine and Immune Systems," pp. 1–464, Pythagora Press, Rome (1989).
74. Ader, R., Felten, D. L., Cohen, N., Eds., "Psychoneuroimmunology, 2nd Edition," pp. 1–1248, Academic Press, San Diego, Calif. (1991).
75. Ader, R., Felten, D., Cohen, N., Interactions between the brain and immune system. Annu. Rev. Pharmacol. Toxicol. 30:561–602 (1990).
76. Stead, R. H., J. Bienenstock, and A. M. Stanisz., Neuropeptide regulation of mucosal immunity. Immunol. Rev. 100:333–359 (1987).
77. Golsteyn, E. J., and Fritzler, M. J., Review: The role of the thymic-hypothalamus-pituitary-gonadal axis in normal immune processes and autoimmunity. J. Rheum. 14:982–990 (1987).
78. Physicians' Desk Reference, 46th edition. Medical Economics Data, Montvale, N.J. (1992).
79. Andrews, B. S., Eisenberg, R. A., Theofilopoulos, A. N., Izui, S., Wilson, C. B., McConahey, P. J., Murphy, E. D., Roths, J. B., and Dixon, F. J., Spontaneous murine lupus-like syndromes: Clinical and immunopathological manifestations in several strains. J. Exp. Med. 149:1198–1215 (1978).
80. Theofilopoulos, A. N., and Dixon, F. J., Murine models of systemic lupus erythematosus. Adv. Immunol. 37:269–390 (1985).
81. Gelfand, J. A., Sherins, R. J., Alling, D. W., and Frank, M. M., Treatment of hereditary angioedema with danazol. New Eng. J. Med. 295:1444–1448 (1976).
82. Jonsson, R., Tarkowski, A., and Backman, K., Effects of immunomodulating treatment on autoimmune sialoadenitis in MRL/Mp-lpr/lpr mice. Agents Actions 25:–374 (1988).
83. Smith, H. R., Chused, T. M., and Steinberg, A. D., Cyclophosphamide-induced changes in the MRL-lpr/lpr mouse: Effects upon cellular composition, immune function and disease. Clin. Immunol. Immunopathol. 32:51–61 (1984).
84. Shiraki, M., Fujiwara, M., and Tomura, S., Long term administration of cyclophosphamide in MRL/1 mice. I. The effects on the development of immunological abnormalities and lupus nephritis. Clin. Exp. Immunol. 55:333–339 (1984).
85. Bartlett, R. R., Popovic, S., and Raiss, R. X., Development of autoimmunity in MRL/lpr mice and the effects of drugs on this murine disease. Scand. J. Rheumatol. Suppl. 75:290–299 (1988).
86. Wilson, J. D., and Foster, D. W., eds., "Williams Textbook of Endocrinology," W B Saunders Company, Philadelphia (1985).

87. Knepper, P. A., Collins, J. A., and Frederick, R., Effect of dexamethasone, progesterone, and testosterone on IOP and GAGs in the rabbit eye. Invest. Ophthalmol. Vis. Sci. 26:1093–1100 (1985).
88. Vida, J. A., "Androgens and Anabolic Agents," Academic Press, New York (1969).
89. Cavallero, C., Relative effectiveness of various steroids in an androgen assay using the exorbital lacrimal gland of the castrated rat. Acta Endocrinol. (Copenh.), 55:119–131 (1967).
90. Clark J H , Schrader W T, O'Malley. Mechanisms of action of steroid hormones. In: Wilson J D, Foster D W , eds. Williams Textbook of Endocrinology, W B Saunders, Philadelphia, pp 35–90 (1992).
91. Trapman J, Ris-Stalpers C, van der Korput J A G M, Kuiper G G J M, Faber P W, Romijn J C, Mulder E, Brinkmann A O. The androgen receptor: functional structure and expression in transplanted human prostate tumors and prostate tumor cell lines. J. Ster. Biochem. Mol. Biol. 37:837 (1990).
92. Quarmby V E, Yarbrough W G, Lubahn D B, French F S, Wilson E M. Autologous down-regulation of androgen receptor messenger ribonucleic acid. Mol. Endocr. 4:22 (1990).
93. Simental J A, Sar M, Lane M V, French F S, Wilson E M. Transcriptional activation and nuclear targeting signals of the human androgen receptor. J. Biol. Chem. 266:510 (1991).
94. Wahli W, Martinez E. Superfamily of steroid nuclear receptors: positive and negative regulators of gene expression. FASEB J 5:2243 (1991).
95. Evans RM. The steroid and thyroid hormone receptor superfamily. Science 240:889 (1988 0.
96. Beato M. Gene regulation by steroid hormones. Cell 56:335 (1989).
97. Sar M, Lubahn D B, French F S, Wilson E M. Immunohistochemical localization of the androgen receptor in rat and human tissues. Endocr 127:3180 (1990).
98. Takeda H, Chodak G, Mutchnik S, Nakamoto T, Chang C. Immunohistochemical localization of androgen receptors with mono- and polyclonal antibodies. J. Endocr. 126:17 (1990).
99. Prins G S, Birch L. Immunocytochemical analysis of androgen receptor along the ducts of the separate rat prostate lobes after androgen withdrawal and replacement. Endocr. 132:169 (1993).
100. Myal Y, Robinso D B, Iwasiow B, Tsuyuki D, Wong P, Shiu RPC. The prolactin-inducible protein (PIP/GCDFP-15) gene: cloning, structure and regulation. Mol. Cell. Endocr. 80:165 (1991).
101. Zeitler P, Argente J, Chowen-Breed J A, Clifton D K, Steiner P A. Growth hormone-releasing messenger ribonucleic acid in the hypothalamus of the adult male rat is increased by testosterone. Endocr. 127:1362 (1990).
102. Quarmby V E, Beckman W C, Wilson E M, French F S. Androgen regulation of c-myc messenger ribonucleic acid levels in rat ventral prostate. Mol. Endocr. 1:865 (1987).
103. Persson H, Lievre C A, Soder O, Villar M J, Metsis M, Olson L, Ritzen M, Hokfelt T. Expression of b-nerve growth factor receptor mRNA in Sertoli cells downregulated by testosterone. Science 247:704 (1990).
104. Mooradian A D, Morley J E, Korenman S G. Biological actions of androgens. Endocr. Rev. 8:1 (1987).
105. Quarmby V E, Kemppainen J A, Sar M, Lubahn D B, French F S, Wilson E M. Expression of recombinant androgen receptor in cultured mammalian cells. Mol. Endocr. 4:1399 (1990).
106. Dong Y, Poellinger L, Gustafsson J A, Okret S. Regulation of glucocorticoid receptor expression: evidence for transcriptional and posttranslational mechanisms. Mol. Endocr. 2:1256 (1988).
107. Rocha F J, Wickham L A, Pena J D O, Gao J, Ono M, Lambert R W, Kelleher R S, Sullivan D A. Influence of gender and the endocrine environment on the distribution of androgen receptors in the lacrimal gland. J Steroid Biochem. Mol. Biol. 46:737 (1993).
108. Lambert R W, Kelleher R S, Wickham L A, Vaerman J P, Sullivan D A. Neuroendocrinimmune modulation of secretory component production by rat lacrimal, salivary and intestinal epithelial cells. Invest. Ophthalmol. Vis. Sci. 35:1192 (1993).
109. Sullivan D A, Bloch K J, Allansmith M R. Hormonal influence on the secretory immune system of the eye: androgen control of secretory component production by the rat exorbital gland. Immunology 52:239 (1984).
110. Steinberg A D. Concepts of pathogenesis of systemic lupus erythematosus. Clin. Immunol. Immunopathol. 63:19 (1992).
111. Mountz J D, Gause W C, Jonsson R. Murine models for systemic lupus erythematosus and Sjögren's syndrome. Curr. Opin. Rheumatol. 3:738 (1991).
112. Sibbit W L. Oncogenes, growth factors and autoimmune diseases. Antican Res. 11:97 (1991).
113. Goetzl E J, Sreedharan S P. Mediators of communication and adaptation in the neuroendocrine and immune systems. FASEB J. 6:2646 1992.
114. Robertson S A, Brannstrom M, Seamark R F. Cytokines in rodent reproduction and the cytokine-endocrine interaction. Curr. Opin. Rheumatol. 4:585 (1992).
115. Krueger J, Ray A, Tamm I, Sehgal P B. Expression and function of interleukin-6 in epithelial cells. J. Cell. Biochem. 45:327 (1991).
116. Mantovani A, Bussolino F, Dejana E. Cytokine regulation of endothelial cell function. FASEB J 6:2591 (1992).
117. Firestein G S. Cytokines in autoimmune diseases. Clin. Mol. Asp. Autoimmune Dis. 8:129 (1992).
118. Kroemer G, Martinez A, Cytokines and autoimmune diseases. Clin. Immunol. Immunopath. 61:275 (1991).
119. Dinarello C A. Interleukin-1 and tumor necrosis factor: effector cytokines in autoimmune diseases. Semin. Immunol. 4:133 (1992).
120. Deem R L, Shanahan F, Targan S R. Triggered human mucosal T cells release tumour necrosis factor-alpha and interferon gamma which kill human colonic epithelial cells. Clin. Exp. Immunol. 83:79 (1991).
121. Mountz J D, Edwards C K. Murine models of autoimmune disease. Curr. Opin. Rheum. 4:621 (1992).
122. Sarvetnick N, Fox H. S. Interferon-gamma and the sexual dimorphism of autoimmunity. Mol. Biol. Med. 7:323 (1990).
123. Wakefield D, Lloyd A. The role of cytokines in the pathogenesis of inflammatory eye disease. Cytokine 4:1 (1992).
124. Rosenbaum J R, Cytokines: the good, the bad, and the unknown. Invest. Ophthalmol. Vis. Sci. 34:2389 (1993).
125. Fox R I, Kang H I, Pathogenesis of Sjögren's syndrome. Rheum Dis. Clin. NA 18:517 (1992).
126. Sullivan D A. Possible mechanisms involved in the reduced tear secretion in Sjögren's syndrome. In: Proceedings of the IVth Int. Symposium on Sjögren's Syndrome. Amsterdam, Kluger Press, 1993.
127. Koh K, Sawada S, fox R I. High levels of IL-10 and Th1 cytokine mRNA transcript in salivary gland biopsies from Sjögren's syndrome patients. In: Proceedings of the IVth International Symposium on Sjögren's Syndrome. Amsterdam, Kluger Press, 1993.

128. Saito I, Terauchi K, Shimuta M, Nishiimura S, Yoshino K, Takeuchi T, Tsubota K, Miyasaka N. Expression of cell adhesion molecules in the salivary and lacrimal glands of Sjögren's syndrome. J. Clin. Lab. Anal. 7:180 (1993).

129. Dang H, Lazaridis K, Aufdemorte T, McGuff H, Talal N. PCR analysis of cytokines produced in salivary glands of Sjögren's syndrome. In: Proceedings of the IVth International Symposium on Sjögren's Syndrome. Amsterdam, Kluger Press, 1993.

130. Skopouli F N, Boumba D, Moutsopoulos H M. Cytokine m-RNA expression in the labial salivary gland tissues from patients with primary Sjögren's syndrome (pSS). In: Proceedings of the IVth International Symposium on Sjögren's Syndrome. Amerstam, Kluger Press, 1993.

131. Ono M, Yoshino K, Tsubota K, Saito I. Subclass expression of IgA in lacrimal glands of patients with Sjögren's syndrome. In: Lacrimal Gland, Tear Film and Dry Eye Syndromes: Basic Science and Clinical Relevance. Adv. Exp. Med. Biol. 1993.

132. Konttinen Y T, Hukkanen M, Kemppinen P, Segerberg M, Sorsa T, Maimstrom M, Rose S, Itescu S, Polak J M. Peptide-containing nerves in labial salivary glands in Sjögren's syndrome. Arth Rheum 35:815 (1992).

133. Collins S M, Hurst S M, Main C, Stanley E, Khan I, Blennerhassett P, Swain M. Effect of inflammation of enteric nerves. Cytokine-induced changes in neurotransmitter content and release. Ann NY Acad. Sci. 664:415 (1992).

134. De M, Sanford T R, Wood G W. Interleukin-1, interleukin-6, and tumor necrosis factor α are produced in the mouse uterus during the estrous cycle and are induced by estrogen and progesterone. Der. Biol. 151:297 (1992).

135. Homo-Delarche F, Fitzpatrick F, Christeff N, Nunez E A, Bach J F, Dardenne M. Sex steroids, glucocorticoids, stress and autoimmunity. J. Ster. Biochem. Mol. Biol. 40:619 (1991).

136. Nagy E, Berczi I, Sabbadini E. Endocrine control of an immunoregulatory cytokine of the submandibular gland. Hans Selye Symposium in Neuroendocrinology, Budapest, p. 51 (1992).

137. Suemori S, Ciacci C, Podolsky D K. Regulation of transforming growth factor expression in rat intestinal epithelial cells. J. Clin. Invest. 87:2216 (1991).

138. Fox R I, Saito I. Sjögren's syndrome: immunologic and neuroendocrine mechanisms. In: Lacrimal Gland, Tear Film and Dry Eye Syndromes: Basic Science and Clinical Relevance. Adv. Exp. Med. Biol. 1993.

139. Shull M M, Ormsby I, Kier A B, Pawlowski S, Diebold R J, Yin M, Allen R, Sidman C, Proetzel G, Calvin D, Annunziata N, Doetschman T. Targeted disruption of the mouse transforming growth factor-$\beta 1$ gene results in multifocal inflammatory disease. Nature 359:693 (1992).

140. Turner M, Chantry D, Katsikis, Berger A, Brennan F M, Feldmann M. Induction of the interleukin 1 receptor antagonist protein by transforming growth factor-$\beta$. Eur. J. Immunol. 21:1635 (1991).

What is claimed is:

1. A method for treating keratoconjunctivitis sicca (KCS) comprising providing a therapeutic agent comprising a therapeutically effective amount of TGF-$\beta$ in a pharmaceutically acceptable carrier substance appropriate for ocular administration, and administering said therapeutic agent locally to the ocular surface or immediate vicinity of an eye of a patient suffering from said KCS.

2. The method of claim 1 wherein in said administering step, said therapeutic agent is applied to the ocular surface of the eye.

3. The method of claim 1 wherein in said administering step, said therapeutic agent is applied to a region of the eye adjacent the ocular surface.

4. The method of claim 3 wherein in said administering step, said therapeutic agent is administered locally by injection.

* * * * *

UNITED STATES PATENT AND TRADEMARK OFFICE
CERTIFICATE OF CORRECTION

PATENT NO. : 5,688,765
DATED : November 18, 1997
INVENTOR(S) : David A. Sullivan It is certified that error appears in the above-indentified patent and that said Letters Patent is hereby corrected as shown below:

In the Title, Title page, and Column 1, line 3, "ANDROGENSOR" should read --ANDROGENS OR--.

Column 3, line 3, "dysfunctions. in" should read --dysfunctions in--.

Column 5, line 16, "MRn/etc." should read --MRL/etc.--.

Column 6, line 53, "antiinflammatoryactivity" should read --antiinflammatory activity--.

Column 6, line 58, "sytemicor" should read --systemic or--.

Column 12, line 4, "innerration" should read --innervation--.

Column 12, line 27, "inflammatoryaction" should read --inflammatory action--.

Column 14, line 33, "(i) orymetholone" should read --(i) oxymetholone--.

Column 14, line 36, "methyl testosterone" should read --methyltestosterone--.

Column 17, line 27, "Donebower" should read --Donehower--.

Column 18, line 12, "yon" should read --von--.

Column 19, line 9, "Waggle" should read --Waggie--.

UNITED STATES PATENT AND TRADEMARK OFFICE
CERTIFICATE OF CORRECTION

PATENT NO. : 5,668,765
DATED : November 18, 1997
INVENTOR(S) : David A. Sullivan It is certified that error appears in the above-indentified patent and that said Letters Patent is hereby corrected as shown below:

Column 19, line 45, "Bobnet" should read --Bohnet--.

Column 23, line 25, "Maimstrom" should read --Malmstrom--.

Signed and Sealed this

Thirtieth Day of November, 1999

Attest:

Q. TODD DICKINSON

Attesting Officer

Acting Commissioner of Patents and Trademarks